US00PP19373P2

(12) United States Plant Patent
Carruth

(10) Patent No.: US PP19,373 P2
(45) Date of Patent: Oct. 21, 2008

(54) HYBRID TEA ROSE PLANT NAMED 'WEKFRANCOLY'

(50) Latin Name: *Rosa hybrida*
Varietal Denomination: WEKfrancoly

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 11/985,661

(22) Filed: Nov. 16, 2007

(51) Int. Cl.
*A01H 5/00* (2006.01)

(52) U.S. Cl. ..... Plt./140

(58) Field of Classification Search ..... Plt./140
See application file for complete search history.

(56) References Cited

U.S. PATENT DOCUMENTS

PP5,519 P 7/1985 McGredy, IV
PP13,513 P2 1/2003 Carruth

*Primary Examiner*—Annette H Para
*Assistant Examiner*—S. B. McCormick-Ewoldt
(74) *Attorney, Agent, or Firm*—McKee, Voorhees & Sease, P.L.C.

(57) ABSTRACT

A new variety of Hybrid Tea rose suitable for garden decoration, having flowers of lasting red coloration.

1 Drawing Sheet

Classification: The present invention relates to a new *Rosa hybrida* plant.

Variety denomination: The new plant has the varietal denomination 'WEKfrancoly'.

BACKGROUND OF THE INVENTION

This invention relates to a new and distinct variety of Hybrid Tea Rose. It has as its seed parent the variety known as 'WEKsanpoly' (U.S. Plant Pat. No. 13,513) and as its pollen parent the variety known as 'MACauck' (U.S. Plant Pat. No. 5,519).

SUMMARY OF THE INVENTION

Among the features which distinguish the new variety from other presently available and commercial rose cultivars known to the inventor are the following combinations of characteristics: its even red coloration that last throughout the life of the flower, its bright red styles, its green-white streak at the midrib of the outermost petals and its red suffusion on the inner surface of the sepal that appears as the flower ages. The plants has an upright to somewhat rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKfrancoly' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKsanpoly' by the following combination of characteristics: whereas 'WEKfrancoly' bears large sized (about 11 to about 15 cm. in diameter) double flowers (about 27 to 32 petals), 'WEKsanpoly' bears significantly smaller flowers (about 6.5 to about 9.0 cm. in diameter) with significantly lesser petalage (about 18 to 26 petals). The new variety is classified as a hybrid tea rose with an upright to somewhat rounded medium height growing habit (about 100 to about 125 cm. in height), whereas the seed parent is classified as a floribunda rose with a significantly smaller rounded bushy to somewhat upright growing habit (about 88 to about 105 cm. in height).

The new variety may be distinguished from its pollen parent, 'MACauck' by the following combination of characteristics: whereas, 'WEKfrancoly' bears double flowers (about 27 to 32 petals) of lasting red coloration sometimes with a green-white streak at the midrib of the outermost petals, 'MACauck' bears double flowers of brilliant lasting red coloration with significantly heavier petalage (about 32 to 37 petals). The new variety has an upright to somewhat rounded medium height growing habit (about 100 to about 125 cm. in height), whereas the pollen parent has a bushy significantly taller and more upright growing habit.

COMPARISON WITH THE CLOSEST COMMERCIALLY AVAILABLE CULTIVAR

The closest commercially available cultivar to the new variety is the seed parent 'WEKsanpoly'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

BOTANICAL DESIGNATION

The new variety botanical designation is *Rosa hybrida* 'WEKfrancoly'.

FLOWER

The new variety usually bears its flowers singly, sometimes in clusters of two to three per stem. Flowers may be borne in irregular somewhat rounded clusters on medium strong medium to long stems (about 16 to about 23 cm.). Outdoors, the plant blooms abundantly and nearly continuously during the growing season. The flowers have a slight tea fragrance.

BUD

The peduncle is about 6.5 to about 9.0 cm. in length, of slender to average caliper (about 0.3 to about 0.5 cm. in diameter), and usually erect to sometimes slightly bending. It is somewhat rough, with some stipitate glands and few small prickles. Peduncle color is between 144A and 146B sometimes moderately suffused with between 183B and 183D.

Before the calyx breaks, the bud is about 2.2 to about 2.6 cm. in diameter at the widest point, about 3.0 to about 3.5 cm. in length, and pointed to ovoid in shape. The surface of the bud bears few foliaceous appendages and stipitate glands, usually with slender somewhat cut foliaceous parts extending beyond the tip of the bud about ½ or more of its length. Bud color is between 144A and 146B sometimes lightly suffused with between 183B and 183D.

The sepals are about 3.8 to about 4.6 cm. in length and about 0.8 to about 1.1 cm. in width at the widest point. The outer surface color of the sepal is between 144A and 146B sometimes lightly suffused with between 183B and 183D.

The inner surface color of the sepal is between 144B and 147C sometimes lightly suffused, especially on the area exposed to the sun, with between 187C and 187D. The sepals are covered and edged with fine wooly tomentum; sepal margins are lined with some stipitate glands and hairs.

The receptacle of the flower is of somewhat short to medium length (about 0.8 to about 1.1 cm.) and average in caliper (about 0.9 to about 1.2 cm. in diameter). The receptacle is moderately rounded to somewhat globular in form. Its surface is very smooth with moderately thick fleshy walls. The receptacle color is between 144A and 146B.

As the petals open (after the calyx breaks), the bud is about 3.3 to about 3.9 cm. in diameter at the widest point, about 4.2 to about 4.8 cm. in length, and somewhat flat-topped to moderately ovoid in form. The color of the under surfaces of the newly opened petals is between 53A and 46A. At the point where the petal attaches, there is a very small zone of near 2B. The color of the upper surfaces of the newly opened petals is between 46A and 53A, sometimes streaked at the midrib of the petal with near 157B. At the point where the petal attaches, there is a moderately small zone of near 2B.

BLOOM

When fully open, the bloom ranges from about 11 to about 15 cm. in diameter. Petalage is double with about 27 to 32 petals and about 3 to 7 petaloids irregularly arranged. When partially open, the bloom form is somewhat cupped to high centered, and the petals are moderately spiraled to cupped with petal edges somewhat reflexed outward. When fully open, the bloom form is more flat to cupped, and the petals are more cupped to undulated with petal edges somewhat reflexed outward.

PETALS

The substance of the petals is moderately heavy and of medium thickness, with upper surfaces very velvety to somewhat satiny and under surfaces slightly shiny to matte. The petals are about 4.7 to about 5.2 cm. in length and about 5.4 to about 5.8 cm. in width at the widest point. Petal margins are mostly entire.

The outer petals are nearly round to broadly ovate in shape with very rounded apices.

The inner petals are nearly round to broadly obovate in shape with rounded apices.

Petaloids are about 2.9 to about 4.6 cm. in length and about 0.8 to about 1.8 cm. in width at the widest point. Petaloids are irregularly shaped to narrowly obovate with somewhat rounded apices.

NEWLY OPENED FLOWER

The under surface color of the outer, intermediate and inner petals is between 46A and 53B. At the point where the petal attaches, there is a very small zone of near 5B. The upper surface color of the outer, intermediate and inner petals is between 46A and 45A. At the point where the petal attaches, there is a moderately small zone of near 5B.

The upper surface of the outermost petals is sometimes streaked at the midrib of the petal with near 157B.

The under and upper surface color of the petaloids are similar in coloration to the upper and under surfaces of the intermediate and inner petals.

The general tonality of the newly opened flower is between 46A and 45A.

THREE-DAY-OLD FLOWER

The under surface color of the outer, intermediate and inner petals is between 53A and 53B. At the point where the petal attaches, there is a very small zone of near 5D. The upper surface color of the outer, intermediate and inner petals is between 46A and 45A. At the point where the petal attaches, there is a moderately small zone of near 5D.

The upper surface of the outermost petals is sometimes streaked at the midrib of the petal with near 157C.

The under and upper surface color of the petaloids are similar in coloration to the upper and under surfaces of the intermediate and inner petals.

The general tonality of the three day old flower is between 46A and 45A.

On the spent bloom, the petals usually drop off cleanly.

In November in Pomona, Calif. blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 85) and are arranged regularly about the pistils; a few are mixed with the petaloids. The filaments are varying in length (about 0.4 to about 1.2 cm.) most with anthers. Filament color is near 9B at the base suffusing to near 28B on the remaining surface. The anthers are of somewhat small to medium size for the class and all open approximately at the same time. Anther color when immature is near 24B on the external part and near 18A on the internal part. Anther color at maturity is near 24A on the external part and near 165A on the internal part. Pollen is moderate to abundant and near 24A in color.

FEMALE REPRODUCTIVE ORGANS

Pistils vary in number (average about 65). The styles are somewhat uneven, moderately short in length (about 0.4 to about 0.7 cm.), somewhat thin to average in caliper, and moderately bunched. Stigma color is near 18C. Style color is near 46A. Ovaries are usually all enclosed in the calyx.

Hips are moderately short to average in length (about 1.4 to about 1.8 cm.), somewhat ovoid to globular in form, and between 163A and 167C in color when ripe. The hip surface is very smooth with moderately thick fleshy walls. The sepals are moderately permanent and usually straight in shape.

The seeds are irregularly rounded, smooth in texture, approximately 8 to about 14 per hip, about 0.5 to about 0.7 cm. in diameter at the widest point and near 163D in color.

FOLIAGE

The compound leaves are usually comprised of three to five leaflets and are borne in normal quantities. The five-leaflet leaves are about 12 to about 14 cm. in length and about 8.8 to about 9.7 cm. in width at the widest point, moderately heavy in texture, and somewhat semi-glossy to matte in finish. The terminal leaflets are about 5.0 to about 5.5 cm. in length and about 3.4 to about 3.9 cm. in width at the widest point, oval in shape with acute apices and somewhat rounded to acute bases. Their margins are usually simply serrate.

The upper surface color of the mature leaf is between 147A and 146A. The under surface color of the mature leaf is between 147C and 147D. The upper surface color of the young leaf is between 147B and 146B, usually moderately suffused with between 183C and 187C. The under surface color of the young leaf is between 147B and 146B, usually heavily suffused with between 183A and 187B.

The rachis is average in caliper and very smooth. The upper side is moderately grooved with some stipitate glands on the edges of the grooves. The under side of the rachis is very smooth with very few hairs and stipitate glands. The rachis color is between 144C and 146C on the under and upper side. The upper side is sometimes moderately heavily washed with between 183A and 187B.

The stipules are about 0.3 to about 0.6 cm. in length and of somewhat narrow to medium width (about 0.4 to about 0.5 cm.) with moderately short straight points that usually turn out at an angle of more than 45 degrees. The stipule color is between 144C and 146C.

The petiole is average in caliper and very smooth. The upper side is moderately grooved with some stipitate glands on the edges of the grooves. The under side of the petiole is very smooth with very few hairs and stipitate glands. The petiole is about 0.2 to about 0.3 cm. in length and about 0.1 to about 0.2 cm in diameter at the widest point. The petiole color is between 144C and 146C on the under and upper side. The upper side is sometimes moderately heavily washed with between 183A and 187B.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright to somewhat rounded medium height growing habit (about 100 to about 125 cm. in height and about 70 to about 85 cm. spread at the widest point), with moderately full branching. It displays moderately vigorous growth and the canes are of medium caliper for the class.

The color of the major stems is between 146B and 148A. They bear several large prickles that are about 0.5 to about 0.8 cm. in length. The large prickles are almost straight and angled moderately downward with a medium length somewhat narrow oval base; prickle color is near 164C. The major stems bear very few small prickles of similar shape and coloration.

The color of the branches is between 144A and 146A sometimes moderately lightly suffused with between 183C and 187C. They bear several large prickles which are of similar size and shape to the large prickles on the major stems; prickle color is near 165B. The branches bear very few small prickles of similar shape and coloration.

The color of the new shoots is between 144C and 146C often moderately heavily suffused with between 183C and 187C. They bear several large prickles which are of similar size and shape to the large prickles on the major stems; prickle color is near 183B. The shoots bear few small prickles of similar shape and coloration.

I claim:

1. A new and distinct Hybrid Tea rose plant of the variety substantially as described and illustrated herein.

* * * * *

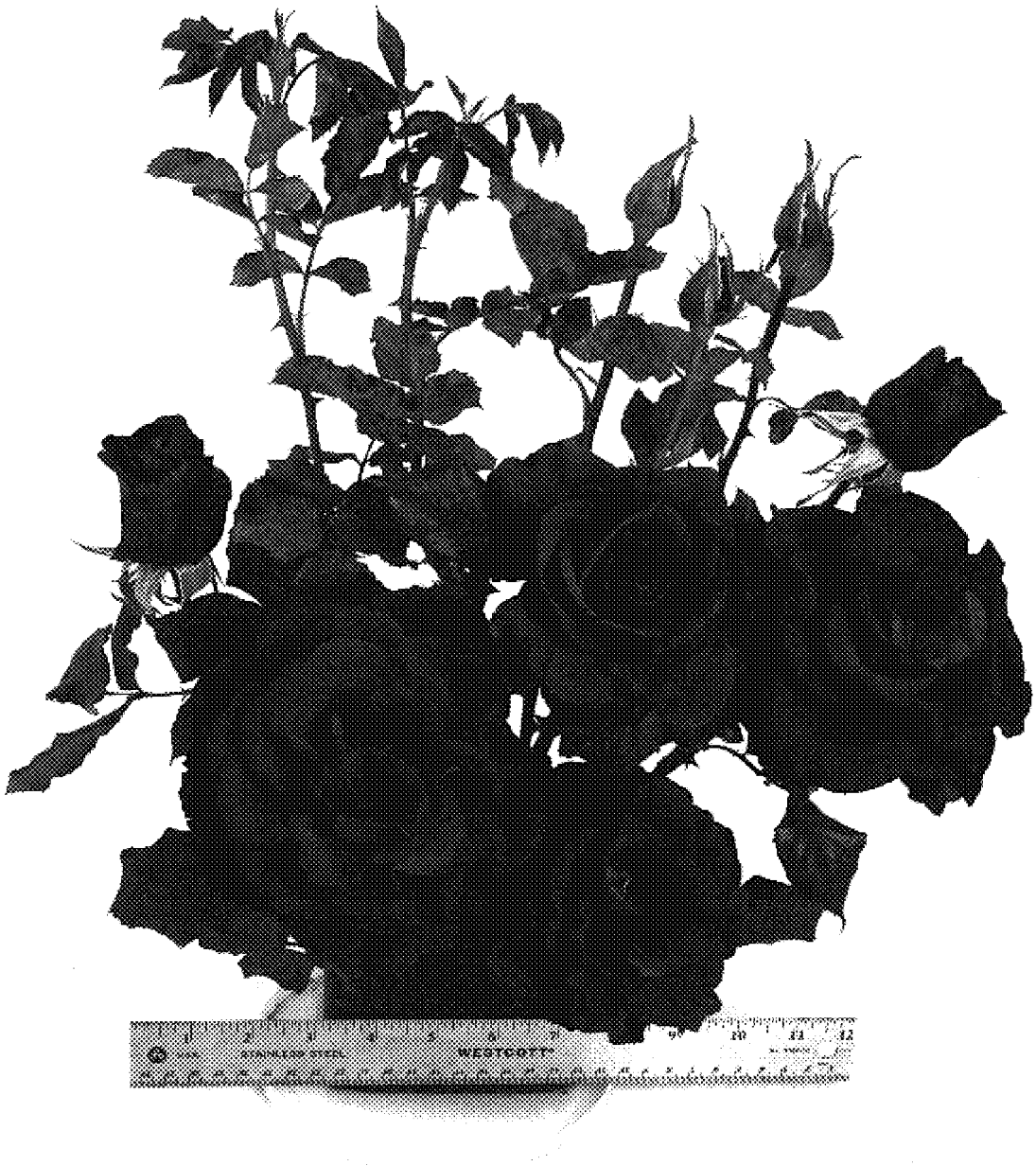
WESTCOTT